United States Patent

Lee et al.

(10) Patent No.: US 6,815,567 B2
(45) Date of Patent: Nov. 9, 2004

(54) DERIVATIVES OF 4-SULFANYLALKYL-3,5-DINITROBENZYL ALCOHOL AND METHOD FOR PREPARING THE SAME

(75) Inventors: Hyoyoung Lee, Daejon-Shi (KR); Mun Seok Jeong, Jeollabuk-do (KR); Sung Yool Choi, Daejon-Shi (KR); Tae Hyoung Zyung, Daejon-Shi (KR)

(73) Assignee: Electronics and Telecommunications Research Institute, Daejon (KR)

( * ) Notice: Subject to any disclaimer, the term of this patent is extended or adjusted under 35 U.S.C. 154(b) by 0 days.

(21) Appl. No.: 10/727,611

(22) Filed: Dec. 5, 2003

(65) Prior Publication Data

US 2004/0147786 A1 Jul. 29, 2004

(30) Foreign Application Priority Data

Jan. 27, 2003 (KR) .................. 10-2003-0005174

(51) Int. Cl.$^7$ .................. C07C 319/00; C07C 205/00
(52) U.S. Cl. .................. 568/932; 568/44
(58) Field of Search .................. 568/932, 44

(56) References Cited

U.S. PATENT DOCUMENTS 4,833,693 A   5/1989   Eyuboglu

OTHER PUBLICATIONS

Guozhu Long, et al; "The LMS Algorithm with Delayed Coefficient Adaptation"; IEEE Transaction on Acoustics, Speech, and Signal Processing; vol. 37., No. 9; Sep. 1989; pp. 1397–1450.

M. Vedat EyuboGlu; "Detection of Coded Modulation Signals on Linear, Severley Distorted Channels Using Decision–Feedback Noise Prediction with Interleaving"; IEEE Transactions on Communications; Vo. 36, No. 4; Apr. 1988; pp. 401–409.

*Primary Examiner*—Paul J. Killos
(74) *Attorney, Agent, or Firm*—Piper Rudnick LLP

(57) ABSTRACT

The present invention is directed to a novel 4-sulfanylalkyl-3,5-dinitro benzyl alcohol compound and its preparation method, more specifically, derivatives of 4-sulfanylalkyl-3, 5-dinitro benzyl alcohol compound having the following formula 1 and its preparation method:

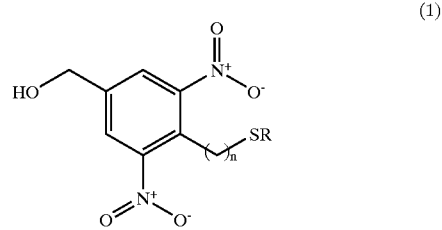

wherein, R is hydrogen, alkyl group, or acetyl group, and n is an integer of 1 to 25. The organic compound of the present invention can be used as a material for molecular electronic device.

13 Claims, No Drawings

DERIVATIVES OF 4-SULFANYLALKYL-3,5-DINITROBENZYL ALCOHOL AND METHOD FOR PREPARING THE SAME

BACKGROUND

1. Field of the Invention

The present invention is directed to novel derivatives of 4-sulfanylalkyl-3,5-dinitro benzyl alcohol, i.e. novel compound having sulfanylalkyl group at 4 position of 3,5-dinitro-benzyl alcohol and its preparation method. The novel compound according to the present invention may be used in manufacturing of molecular electronic device.

2. Discussion of Related Art

A molecular electronic device is basically made up of two electrodes and organic molecules covalently bonded to the electrodes, the organic molecule structures function as individual molecule which is separated from the bulk solid state, and the energy level accessible at the molecular state is quantized. Up to the present, the researches on development of organic materials required for the molecular electronic device are concentrated on the materials for molecular wire, molecular switch and molecular rectifier, and the researches have been conducted in developed countries such as America and Europe. Especially, the development of materials for molecular rectifier provided the primitive initiation for the need of development of materials for molecular electronic device. In 1974, Aviram and Ratner of IBM, an American company, proposed at first time that devices having molecular diode rectifying characteristics can be made using the properties of organic molecules, that is, organic molecules themselves have size of nanometer as well as semi-conductive properties at ambient temperature (Chem. Phys. Lett. 1974, 29, 277). They proposed that when a molecule has both of electron donor group(D) and electron acceptor group(A) which are linked through σ-bond, the molecule may be polarized and may have direction, therefore, current will flow to one direction when between a pair of metal electrode, these molecules were aligned in one direction and made an electric circuit. Mattern group approved this hypothesis in 1999 by an experiment for verification of rectifying property of organic LB film formed between two electrodes(Journal of material chemistry, 1999, 9, 2271–75). Furthermore, Metzger group confirmed that compounds linked by π-bond, as well as σ-bond, also has rectifying property(J. Am. Chem. Soc. 1997, 119, 10455). In addition, professor M. A. Reed, et al of Yale University reported that organic material without electron donor and electron acceptor group may also have rectifying diode property using potential difference of metal(for example, Au and Ti electrode)(Appl. Phys. Lett. 1997, 71, 611).

However, in spite of the variety of researches on development for rectifying diode device using the properties of organic molecules, up to now, the question that whether rectifying property of molecular electronic device is based on the property of organic material or based on other factors is not explained clearly. Thus, there is a request for a development of novel molecular rectifying material by which rectifying property of molecular electronic device can be explained fundamentally. When novel molecular electron accepting organic material is developed and the property of the developed material is measured, it is considered that molecular electronic device having organic material between two electrodes can provide an information on rectifying property and rectifying direction which are depend on the property of the organic material. It is expected that the rectifying property of the organic material can be determined by measuring current-voltage relationship or current flow direction of a device made by forming SAM (self-assembled mono-layer) on one electrode and forming the another electrode on the other side of SAM, or by measuring current-voltage relationship or current flow direction of a SAM using CP-AFM(conducting probe atomic force microscopy) or STM (scanning tunneling microscopy).

However, up to present, there is no report on the organic materials that can attach molecular electron accepting organic material to the electrode. One of the main reasons why there is no such report is the difficulty in synthesis of organic materials for introducing alligator clip to an end of molecular electron acceptor group.

SUMMARY OF THE INVENTION

The present invention is directed to novel derivatives of 4-sulfanylalkyl-3,5-dinitro-benzyl alcohol having structure represented by the following formula 1:

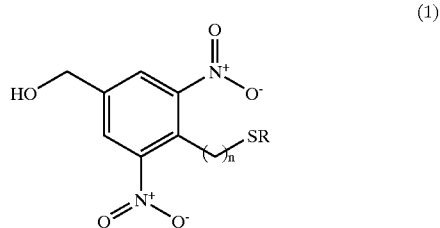

(1)

wherein, R is hydrogen, alkyl group, or acetyl group, and n is an integer of 1 to 25. In the novel derivatives of the present invention, to introduce a sulfur atom that is necessary in forming SAM, a sulfanylalkyl group is introduced at 4 position of 3,5-dinitro-benzyl alcohol, which has been used as molecular electron acceptor.

The present invention is also directed to a method for preparing a compound of formula 1, comprising the steps of a) preparing p-methyl-3,5-dinitro benzoic acid by reacting p-methyl benzoic acid with nitric acid;

b) preparing alkyl 4-methyl-3,5-dinitrobenzoate by reacting said p-methyl-3,5-dinitro benzoic acid with alkyl alcohol in the presence of a catalyst;

c) preparing alkyl 4-halomethyl-3,5-dinitrobenzoate by reacting said alkyl 4-methyl-3,5-dinitrobenzoate with N-halosuccinimide;

d) preparing alkyl 4-halomethyl-3,5-dinitrobenzyl alcohol by converting ester group of alkyl 4-halomethyl-3,5-dinitrobenzoate to alcohol group in the presence of catalyst;

e) preparing compound of following formula wherein R is acetyl group or alkyl group by reacting said alkyl 4-halomethyl-3,5-dinitrobenzyl alcohol with potassium thioacetate or alkylthio sodium, or preparing compound of following formula wherein R is hydrogen by further removing acetyl group or alkyl group.

DETAILED DESCRIPTION OF PREFERRED EMBODIMENTS

As a results of the successive researches to achieve the objects of the present invention, it has now been found that novel compound of present invention was successfully synthesized by introducing 4-sulfanylalkyl group into 4 position of 3,5-dinitro-benzyl alcohol. The novel derivatives of 4-sulfanylalkyl-3,5-dinitro-benzyl alcohol of the present invention can be represented by a chemical formula 1, as follow:

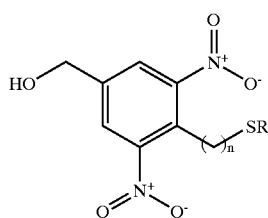
(1)

wherein, R is hydrogen, alkyl group, or acetyl group, and n is an integer of 1 to 25.

Preferably, R is hydrogen, linear or branched alkyl group having 1 to 6 carbon atoms, or acetyl group, and n is an integer of 1 to 6.

More preferably, R is hydrogen, linear or branched alkyl group having 1 to 3 carbon atoms, or acetyl group, and n is an integer of 1 to 3.

Most preferably, R is an acetyl group, and n is an integer of 1.

A method for preparing the compounds having structure represented by the formula 1, wherein said method is composed of multi-step reaction introducing alkyl group including thioalkyl group to 3,5-dinitrobenzyl alcohol, is also provided by the present invention.

A method for preparing a derivatives of 4-sulfanylalkyl-3,5-dinitro-benzyl alcohol of present invention comprises the steps of:
a) preparing p-methyl-3,5-dinitro-benzoic acid by reacting p-methyl benzoic acid with nitric acid;
b) preparing alkyl 4-methyl-3,5-dinitrobenzoate by reacting said p-methyl-3,5-dinitro-benzoic acid with alkyl alcohol in the presence of a catalyst;
c) preparing alkyl 4-halomethyl-3,5-dinitrobenzoate by reacting said alkyl 4-methyl-3,5-dinitrobenzoate with N-halosuccinimide;
d) preparing alkyl 4-halomethyl-3,5-dinitrobenzyl alcohol by converting ester group of alkyl 4-halomethyl-3,5-dinitrobenzoate to alcohol group in the presence of catalyst;
e) preparing compound of following chemical formula 1 wherein R is acetyl group or alkyl group by reacting said alkyl 4-halomethyl-3,5-dinitrobenzyl alcohol with potassium thioacetate or alkylthio sodium, or preparing compound of following chemical formula 1 wherein R is hydrogen by further removing acetyl group or alkyl group:

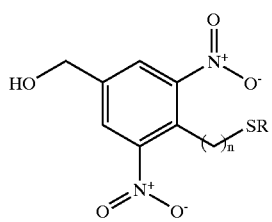
(1)

wherein, R is hydrogen, alkyl group, or acetyl group, and n is an integer of 1 to 25.

The method for preparing the derivatives of the formula 1 according to the present invention is represented in the following equation 1:

[Equation 1]

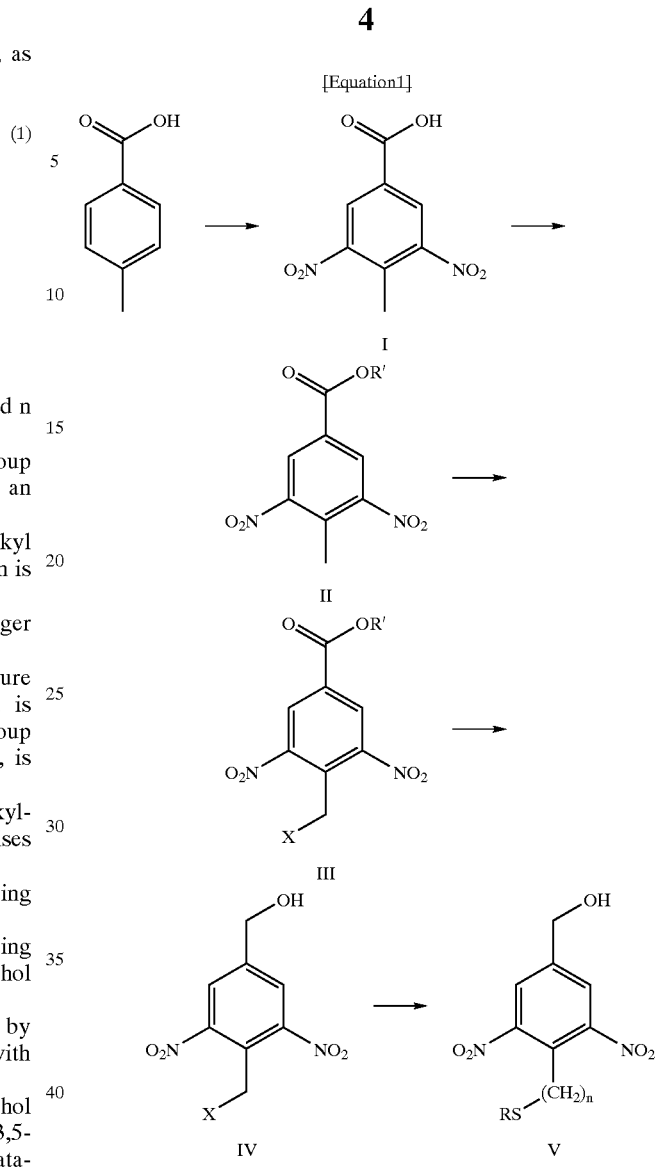

wherein, R is hydrogen, alkyl group, or acetyl group, n is an integer of 1 to 25, and X is halogen atom.

Alkyl 4-methyl-3,5-dinitrobenzoate(Compound I) can be prepared from p-methyl benzoic acid. The reaction uses nucleophilic reaction principle wherein electron-rich aromatic benzene attacks electron-poor nitro group. In the above reaction, two nitro groups are attached nearby the methyl group since methyl group of p-methyl benzoic acid gives electrons more easily than carboxyl group. Compound II is prepared by introducing ester group to protect the carboxyl group of resulting compound I. compound III can be prepared by introducing halogen at 4-methyl position using radical reaction condition. Compound IV can be prepared by reducing the ester group into alcohol group by adding metal hydride at low temperature. Final objective compound V can be obtained by substituting halogen atom with thioester group. The steps of the method for preparing the derivatives of the formula 1 according to the present invention are described in more detail.

A) Preparation of Compound I (Step a)

p-methyl-3,5-dinitro benzoic acid of compound I may be synthesized from the reaction of p-methyl benzoic acid with 60–65% nitric acid in the presence of a catalyst. Generally, the reaction may be conducted at a temperature of 0 to 40° C., preferably 20 to 25° C., for 2 to 3 hours, with sufficient agitation. The mole ratio of nitric acid is in the range from 2 to 4 moles, preferably 2 to 2.2 moles per mole of p-methyl benzoic acid. Any solvent that doesn't deteriorate the reaction can be used. Water is preferable solvent. Strong acid, preferably 95–99% sulfuric acid can be used as catalyst.

B) Preparation of Compound II (Step b)

To protect a carboxyl group of p-methyl-3,5-dinitro benzoic acid prepared, alkyl 4-methyl-3,5-dinitro benzoate (Compound II) can be prepared by esterification reaction. Although strong acid or weak base may be used as catalyst for introduction of ester group, a method using strong acid catalyst requires severe condition under which decomposition of unstable groups of the compound may be occurred. Thus, in the present invention, weak base that requires very mild condition is used as catalyst, in order to prevent deformation of other groups of the compound. Pyridine-based compound, preferably 4-dimethylaminopyridine and 1,4-dicyclohexylcarbodiimide may be used as base catalyst in the step b of present invention. The amount of catalyst is in the range from 1 to 1.5 moles, preferably 1.1 to 1.3 moles per carboxylic acid. The reaction temperature is suitably in the range of from 0 to 40° C., preferably 20 to 25° C., and the reaction time is in the range of 24 to 36 hours. Any organic solvent that doesn't deteriorate the reaction can be used. Dichloromethane is preferably used.

C) Preparation of Compound III (Step c)

Alkyl 4-halomethyl-3,5-dinitro benzoate(Compound III) may be prepared by substituting one of the three hydrogen at benzyl position of alkyl 4-methyl-3,5-dinitro benzoate prepared in step b with halogen. The reaction is conducted, in a reaction vessel equipped with reflux device, by heating the mixture of alkyl 4-methyl-3,5-dinitro benzoate dissolved in anhydrous carbon tetrachloride solvent, N-halosuccinimide, preferably N-bromosuccinimide, and benzoyl peroxide, by tungsten lamp. Preferably same moles of N-halosuccinimide and benzoyl peroxide, respectively, with respect to the alkyl 4-methyl-3,5-dinitrobenzoate may be added, more preferably additional 0.3 to 0.5 moles of N-halosuccinimide and benzoyl peroxide, respectively, are added during the reaction process. The reaction conditions should be anhydrous in order to prevent the adverse effects of moisture since the reaction mechanism is radical reaction. Therefore, available solvent is preferably anhydrous carbon tetrachloride. The reaction time is suitably 12 to 14 hours. The reaction temperature is around the boiling point of solvent used as reaction medium, preferably, around the boiling point of carbon tetrachloride that is most commonly used as solvent for radical reaction.

D) Preparation of Compound IV (Step d)

Ester group of alkyl 4-halomethyl-3,5-dinitro benzoate is converted into alcohol group by use of metal hydride. Any metal hydride, preferably metal hydride having relatively weak reactivity, e.g. diisobutyl aluminum hydride may be used. Preferably, 1 to 2 M, more preferably 1.5M of diisobutyl aluminum hydride in anhydrous toluene may be used in the ratio of 2 to 3 moles, more preferably 2.2 to 2.5 moles to the 1 mole of alkyl 4-halomethyl-3,5-dinitro benzoate. The reaction is conducted, maintaining the temperature at about −78° C., by adding slowly the metal hydride over about 10 to 30 minutes, then agitating further 1 hour. Any organic solvent that does not give adverse effects on the reaction, preferably toluene may be used. Anhydrous solvent should be used since metal hydride reacts easily with water and then the metal hydride loses its reactivity. The completion of reaction is verified by a conventional method known to the art, e.g. TLC method. After the completion of reaction, ligand is added to remove unreacted excess metal hydride. For example, tartrate ligand is added to precipitate a metal-tartrate chelate compound and to terminate the reaction.

E) Preparation of Compound V (Step e)

i) Preparation of Substituted 4-sulfanyl-3,5-dinitro Benzyl Alcohol 4-sulfanyl-3,5-dinitro benzyl alcohol is prepared by substituting halogen of alkyl 4-halomethyl-3,5-dinitrobenzyl alcohol with thiol group. To introduce thiol group, metal thiol compound, for example, metal thiol alkyl compound or metal thiol acetyl compound may be used. Metal thiol compound may be used in the range from 1.1 to 1.5 moles, preferably 1.2 mole per 1 mole of alkyl 4-halomethyl-3,5-dinitrobenzyl alcohol. Any organic polar solvent that does not give adverse effects on the reaction, preferably anhydrous organic polar solvent, such as anhydrous alcohol may be used The reaction is conducted at 90° C. to 100° C. for 0.5 to 1.0 hours.

ii) Preparation of Compound V wherein R is Hydrogen by Removing Acetyl Group

Generally, acetyl or alkyl protection groups are introduced to reduce the reactivity of thiol group or to protect the thiol group since the thiol group oxidized easily during the preparation of compounds containing thiol group. Basic ammonium hydroxides are commonly used to remove the acetyl protection group in order to obtain desired thiol compound. Preferably, 25 to 28% ammonium hydroxide is added to a solution of 4-acetylsulfanylalkyl-3,5-initrobenzyl alcohol in anhydrous and oxygen-free tetrahydrofuran(THF) and the mixture is agitated. preferably 1 to 2 moles, preferably 1.2 to 1.5 moles of ammonium hydroxide may be used for 1 mole of thiol compound containing acetyl group. Any organic polar solvent that does not give adverse effects on the reaction, preferably THF may be used as reaction solvent. The reaction is preferably conducted at 20° C. to 30° C. for 0.5 to 1.0 hours. Oxygen-free condition will be preferred before the completion of reaction.

iii) Preparation of Compound V wherein R is Hydrogen by Removing Alkyl Group

Alkyl group will be removed by adding sodium thiomethoxide($CH_3SNa$) to the solution of 4-alkylsulfanylalkyl-3,5-dinitrobenzyl alcohol in dimethylfornamnide(DMF).

Organic solvents having high boiling point, such as dimethylformamide(DMF) or NMP(1-methyl-2-pyrrolidinone) are preferably used. In addition, in stead of sodium thiomethoxide($CH_3SNa$), sodium thioalkyl(RSNa) such as sodium thio i-propyl(i-propyl SNa) or sodium thio tertiary-butyl(t-butyl SNa) may be used. Sodium thiomethoxide, etc may be used in the range of 3 to 6 equivalents, preferably 4 to 5 equivalents per alkyl 4-alkylsulfanylalkyl-3,5-dinitro benzyl alcohol. The reaction is conducted at the temperatures of 150–200° C. for 2 to 5 hours.

Molecular electronic device according to the second object of present invention comprises at least one organic functional layer between one pair of electrode, the organic functional layer comprises aforementioned compound of chemical formula 1. The following examples are given for the purpose of illustrating the invention in more detail.

EXAMPLES (1) Preparation of p-methyl-3,5-dinitro-para-toluic acid (Compound I)

To para-toluic acid(5.0 g, 0.0367 mol) charged in a 200 ml of 2-neck round bottom flask equipped with condenser, dropping funnel and magnetic stirrer and put in a water bath maintained at 20° C., sulfuric acid(50 ml, 95%) and nitric acid(20 ml, 70%) were slowly added over 10 minutes, respectively, in series. The resulting mixture was stirred for 2 hours at ambient temperature, then poured onto ice water (100 ml) to quench the reaction, then yellow solid was formed. The solid was filtered, washed with cold water and dried in an oven over night and 7.96 g(0.0352 mol, yield 96%) of compound I was obtained. Hydrogen and carbon Nuclear magnetic resonance (NMR) spectrum showed that the product has identical structure with 3,5-dinitro-para-toluic acid(compound I).

(2) Preparation of ethyl 4-methyl-3,5-dinitro benzoate (Compound II)

To 3,5-dinitro-para-toluic acid(5.0 g, 0.022 mol) which was obtained in (1), charged in a 500 ml of 2-neck round bottom flask equipped with thermocouple and stirrer and put in a water bath maintained at 20° C., anhydrous ethanol(200 ml) and anhydrous methylene chloride(100 ml) were added. To a resulting mixture solution, 1,4-dicyclohexylcarbodiimide(5.0 g, 0.0243 mol) and 4-dimethylaminopyridine (2.97 g, 0.0243 mol) were added at ambient temperature. The resulting mixture was stirred for 12 hours at ambient temperature. Thereafter, resulting urea of white solid was filtered away and the filtrate was concentrated. The concentrated product was purified on a silica gel chromatography using 3.2% acetone-hexane solvent system and white solid of ethyl 4-methyl-3,5-dinitro benzoate 4.60 g(0.018 mol, yield 82%) was obtained. Nuclear magnetic resonance (NMR) spectrum showed that the product has identical structure with compound II and the NMR data was set forth below.

$^1$H NMR (CDCl$_3$) (ppm): 8.57(2H, s); 4.48(2H, q, J=7.2Hz); 2.63(3H, s); 1.47(3H, t, J=7.0Hz).

$^{13}$C NMR (CDCl$_3$) (ppm): 162.17; 151.22; 131.12; 130.32; 127.55; 62.54; 15.15; 14.17.

(3) Preparation of ethyl 4-bromomethyl-3,5-dinitro benzoate (Compound III)

Anhydrous carbon tetrachloride 100 ml and ethyl 4-methyl-3,5-dinitro benzoate 3.5 g(0.0138 mol) were charged into a 200 ml of 2-neck round bottom flask equipped with condenser, dropping funnel and stirrer and put in an oil bath maintained at 100° C. At ambient temperature, N-bromosuccinimide(2.45 g, 0.0138 mol) and benzoyl peroxide(3.3 mg, 0.0138 mmol) were added and the mixture was refluxed for 5 hours by heating of 500 W Tungsten lamp. Additional N-bromosuccinimide 0.35 g and benzoyl peroxide 3 mg were added and the resulting mixture was heated by 500 W tungsten lamp for 12 hours. Solvent was removed under reduced pressure and then, the resultant was purified on a silica gel chromatography using 2% ethylacetate-hexane solvent system and yellow solid of ethyl 4-bromomethyl-3,5-dinitro benzoate (2.2 g, 6.6 mmol, yield 48%) was obtained. Nuclear magnetic resonance (NMR) spectrum showed that the product has identical structure with compound III and the NMR data was set forth below.

$^1$H NMR (CDCl$_3$) (ppm): 8.66(2H, s); 4.93(2H, s); 4.48 (2H, q, J=7.4Hz); 1.45(3H, t, J=7.2Hz);

$^{13}$C NMR (CDCl$_3$) (ppm): 162.49; 150.70; 133.34; 131.02; 129.54; 63.72; 20.29; 15.01

(4) Preparation of 4-bromomethyl-3,5-dinitrobenzyl alcohol (Compound IV)

Anhydrous toluene 20 ml was charged into a 100 ml 2-neck round bottom flask equipped with stirrer, dried under vacuum by flame and put in a bath containing dry ice in acetone, maintaining −78° C. and having thermocouple, then, ethyl 4-bromomethyl-3,5-dinitro benzoate(2.0 g, 0.006 mol) was dissolved into the toluene in the flask. After cooling the reaction mixture to −78° C., 25 wt %, 1.5M diisobutyl aluminum hydride solution(10 ml, 0.015 mol) in toluene solvent was added slowly to the mixture. While maintaining the temperature at −78° C., the mixture was agitated for 1 hour, the temperature was raised to −50° C., then the degree of reaction was measured by TLC. To end the reaction, aqueous solution of 2N sodium potassium tartrate tetrahydrate(10 ml) was added to the reaction mixture and the mixture was agitated for 12 hours. Reaction product was extracted by methylene chloride, dried on magnesium sulfate and concentrated. Yellow liquid of ethyl 4-bromomethyl-3,5-dinitrobenzyl alcohol (905 mg, 0.0031 mol, yield 52%) was obtained by purification on a silica gel chromatography using 25% ethylacetate-hexane solvent system. Nuclear magnetic resonance (NMR) spectrum showed that the product has identical structure with compound IV and the NMR data was set forth below.

$^1$H NMR (CDCl$_3$) (ppm): 8.08(2H, s); 4.89(2H, s); 4.87 (2H, bs);

$^{13}$C NMR (CDCl$_3$) (ppm): 149.86; 144.73; 125.88; 124.97; 62.42; 20.27.

(5) Preparation of 4-acetylsulfanylmethyl-3,5-dinitrobenzyl alcohol (Compound V)

4-bromomethyl-3,5-dinitro benzyl alcohol(800 mg, 2.75 mmol), anhydrous ethanol(10 ml) and potassium thioacetate (380 mg, 3.3 mmol) were charged into a 200 ml 2-neck round bottom flask equipped with condenser, dropping funnel and stirrer and put in an oil bath maintaining 150° C. and having thermocouple. The resulting mixture solution was heated at 100° C. for 30 minutes and cooled to ambient temperature. White solid formed during the reaction was filtered away and the filtrate was concentrated by removing the solvent under reduced temperature. Pale yellow solid of 4-acetylsulfanylmethyl-3,5-dinitrobenzyl alcohol (710 mg, 2.48 mmol, yield 90%) was obtained by purification on a silica gel chromatography using 20% ethylacetate-hexane solvent system. Nuclear magnetic resonance (NMR) spectrum showed that the product has identical structure with compound V and the NMR data was set forth below.

$^1$H NMR (CD$_3$OD) (ppm): 8.11(2H, s); 4.73(2H, s); 4.55(2H, s); 2.25(3H, s);

$^{13}$C NMR (CD$_3$OD) (ppm): 195.84; 152.26; 146.51; 127.158; 126.73; 63.00; 30.08; 26.50.

In the above examples, only some compounds of present invention are synthesized according to the method of present invention. However, the examples are given only for the purpose of illustrating the present invention and are not construed as limiting the scope of that which is regarded as the invention. Therefore, the scope of the present invention is only to be limited by the following claims and the equivalents thereto.

4-sulfanylalkyl-3,5-dinitrobenzyl alcohol of the present invention can be used as molecular electron accepting material for molecular electronic device in which organic material is positioned between two electrodes since SAM can be formed using the sulfur atom of the thiol group at 4 position of 4-sulfanylalkyl-3,5-dinitrobenzyl alcohol according to the present invention.

Furthermore, the compound of present invention is expected as a material for measurement of current-voltage and determination of current flow direction in a molecular electronic device using CP-AFM(conducting probe atomic force microscopy) or STM(scanning tunneling microscopy) when the compound of present invention was applied as molecular electron accepting organic material having molecular rectifying characteristics.

What is claimed is:

1. A compound of 4-sulfanylalkyl-3,5-dinitrobenzyl alcohol having the following formula 1:

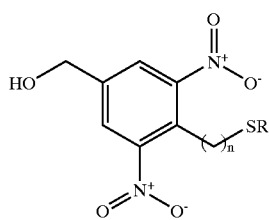

(1)

wherein, R is hydrogen, alkyl group, or acetyl group, and n is an integer of 1 to 25.

2. A compound according to claim 1, characterized in that R is hydrogen, methyl group, or acetyl group.

3. A compound according to claim 2, characterized in that R is acetyl group and n is an integer of 1.

4. A method for preparing a compound of following formula, comprising the steps of
   a) preparing p-methyl-3,5-dinitro benzoic acid by reacting p-methyl benzoic acid with nitric acid;
   b) preparing alkyl 4-methyl-3,5-dinitrobenzoate by reacting said p-methyl-3,5-dinitro benzoic acid with alkyl alcohol in the presence of a catalyst;
   c) preparing alkyl 4-halomethyl-3,5-dinitrobenzoate by reacting said alkyl 4-methyl-3,5-dinitrobenzoate with N-halosuccinimide;
   d) preparing alkyl 4-halomethyl-3,5-dinitrobenzyl alcohol by converting ester group of alkyl 4-halomethyl-3,5-dinitrobenzoate to alcohol group in the presence of catalyst;
   f) preparing compound of following formula wherein R is acetyl group or alkyl group by reacting said alkyl 4-halomethyl-3,5-dinitrobenzyl alcohol with potassium thioacetate or alkylthio sodium, or preparing compound of following formula wherein R is hydrogen by further removing acetyl group or alkyl group:

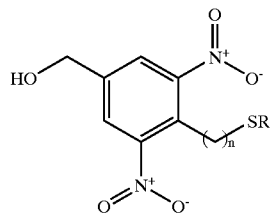

(1)

wherein, R is hydrogen, alkyl group, or acetyl group, and n is an integer of 1 to 25.

5. A method according to the claim 4, characterized in that said alkyl alcohol of step b) is ethyl alcohol.

6. A method according to the claim 4, characterized in that said catalyst of step b) is pyridine-based basic catalyst.

7. A method according to the claim 6, characterized in that said pyridine-based basic catalyst is 4-dimethylaminopyridine or 1,4-dicyclohexylcarbodiimide.

8. A method according to the claim 4, characterized in that said N-halosuccinimide of step c) is N-bromosuccinimide.

9. A method according to the claim 4, characterized in that said catalyst of step d) is metal hydride.

10. A method according to the claim 9, characterized in that said metal hydride is diisobutyl aluminum hydride.

11. A method according to the claim 9, characterized in that remaining of said metal hydride is removed by precipitation of metal-tartrate chelate compound formed by a result of reaction between said metal hydride and tartrate ligand further added to the reaction mixture to end the reaction.

12. A method according to the claim 4, characterized in that, in step e), said compound of formula 1 wherein R is hydrogen is prepared by further reacting the said compound of formula 1 wherein R is acetyl group with ammonium hydroxide.

13. A method according to the claim 4, characterized in that, in step e), said compound of formula 1 wherein R is hydrogen is prepared by further reacting the said compound of formula 1 wherein R is alkyl group with sodium thio methoxide(CH₃SNa), sodium thio iso-propoxide(i-propyl SNa) or sodium thio t-butoxide(t-butyl SNa).

* * * * *